United States Patent
Noguchi et al.

(12) 
(10) Patent No.: US 6,432,535 B1
(45) Date of Patent: Aug. 13, 2002

(54) PIGMENT IN THIN FLAKES AND A METHOD FOR MANUFACTURING THE SAME

(75) Inventors: Tamio Noguchi; Yukitaka Watanabe, both of Fukushima-ken (JP)

(73) Assignee: Merck Patent Geseelschaft mit beschraenkter Haftung (DE)

( * ) Notice: Subject to any disclaimer, the term of this patent is extended or adjusted under 35 U.S.C. 154(b) by 97 days.

(21) Appl. No.: 09/629,150

(22) Filed: Jul. 31, 2000

(30) Foreign Application Priority Data

Jul. 29, 1999 (JP) .......................................... 11-214927

(51) Int. Cl.⁷ ................................................ B32B 5/16
(52) U.S. Cl. ..................... 428/403; 427/212; 427/215; 427/219; 428/404; 524/492; 524/493; 524/497
(58) Field of Search ................................ 428/403, 404; 427/212, 215, 219; 524/492, 493, 497

(56) References Cited

U.S. PATENT DOCUMENTS

| 3,634,119 A | * | 1/1972 | Klenke | 106/291 |
| 3,861,946 A | * | 1/1975 | Waitkins et al. | 117/100 B |
| 4,882,133 A | * | 11/1989 | Saegusa | 423/335 |
| 5,407,746 A | | 4/1995 | Prengel et al. | 428/403 |
| 5,846,310 A | * | 12/1998 | Noguchi et al. | 106/482 |
| 6,113,682 A | * | 9/2000 | Shin et al. | 106/446 |

FOREIGN PATENT DOCUMENTS

EP    0 543 999 B1    8/1991

* cited by examiner

*Primary Examiner*—Hoa T. Le
(74) *Attorney, Agent, or Firm*—Millen, White, Zelano & Branigan

(57) ABSTRACT

A pigment in thin flakes where spherical silica particles having an average particle size of 20–400 nm are adhered on the surface of a flaky substrate having an average particle size of 0.5–10 μm and then the said spherical silica particle-adhered surface of the flaky substrate adhered with spherical silica is further coated with ultrafine particles of titanium dioxide.

16 Claims, 1 Drawing Sheet

PIGMENT IN THIN FLAKES AND A METHOD FOR MANUFACTURING THE SAME

The present invention relates to a pigment in thin flakes for cosmetics, resins, etc. More particularly, the present invention relates to a pigment of thin flakes having a high soft focus effect which is a wrinkle-hiding effect for skin, a good spreading effect on the skin, an ultraviolet shielding effect and an appropriate whiteness degree which are requested to cosmetics and also relates to a method for manufacturing the same.

BACKGROUND OF THE INVENTION

Up to now, substances in thin flakes such as natural mica, synthetic mica, mica coated with titanium oxide, talc, sericite and boron nitride have been used as extenders for cosmetics or fillers for resins, etc. However, when they are used for cosmetics, they do not satisfy the characteristics such as a wrinkle-hiding effect, ultraviolet-shielding effect and degree of whiteness which are required together with adhesive property to and spreading property on the skin.

With regard to a pigment having good spreadability to the skin, extenders such as talc having no luster and boron nitride have been commercially available, but some of talc has been confirmed to contain asbestos and, recently, its use as a pigment for cosmetics has been restricted. Pigments consisting of boron nitride are not suitable for a cosmetic use because boron nitride is expensive and, in addition, unreacted boric acid is sometimes contained in its material. Further, bismuth oxychloride in thin flakes, mica coated with titanium oxide, etc. have been used in some cosmetics as pigments having good spreadability because their feel and spreadability on the skin are good. However, bismuth oxychloride has too strong luster and is unnatural for the skin and, as a result, its use as a foundation, etc. has been limited.

With regard to a pigment having an improved spreadability, one where silica particles of 0.05–50 $\mu$m are adhered on the surface of mica or of mica titanium has been proposed (DE 3922178/1989; the Japanese Laid-Open Patent Publication Hei-03/45660, both corresponding to U.S. Pat. No. 5,407,746. This pigment aims improved spreadability due to a ball bearing effect by silica particles but there is a disadvantage that adhesiveness to the skin is weak and adhesion of the silica particles onto the mica surface is insufficient as well. Thus, exfoliation is apt to occur in the stages after manufacture and before use whereby it is difficult to achieve a sufficient spreading effect. Further, the diameter of the adhered silica particles is as big as 0.05–50 $\mu$m and, therefore, the soft focus effect (refer to Naoki Nakamura, et al: the XIVth I.F.S.C.C. Congress, Barcelona, 1986, volume1, pages 51–63) corresponding to a wrinkle-hiding effect can be hardly expected.

With regard to a pigment wherein the above-mentioned pigment in thin flakes coated with silica particles is improved, pigments in which adhesive property of the spherical silica particles is improved using organic silica such as 4-ethyl silicate or sodium silicate have been proposed (WO 92/03119). It is said that such pigments have improved adhesive property and spreading effect to the skin and have a soft focus effect as well. Diameter of the silica particles disclosed here is mentioned to be about 5 $\mu$m or smaller or, preferably, 0.05–3 $\mu$m. Even in such a particle size however, the silica particles are still big and, therefore, specific treatment to provide adhesive properties is necessary (dielectric constant and ion concentration of the dispersion solution are to be specified to achieve adhesive properties). That is inconvenient for manufacturing. Moreover, since the pigments have a low degree of whiteness, there is another problem that, when used in cosmetics, titanium dioxide or the like must be further added for increasing whiteness.

In addition, in the above-mentioned two types of the pigments coated with silica particles, flaky substrates having particle sizes of as big as 1–500 $\mu$m and about 30 $\mu$m (refer to the Examples), respectively are used and, therefore, they are too big especially for foundations and their sliding on the skin is not good.

SUMMARY OF THE INVENTION

The present inventors have carried out an intensive investigation for improvement especially in the pigment for cosmetics with an object of solving the above-mentioned problems and have succeeded in developing a pigment in thin flakes having a wrinkle-hiding effect (soft focus effect), spreading effect (a product exhibiting a low frictional coefficient or MIU), ultraviolet shielding effect and appropriate whiteness.

Thus, the present invention offers a pigment comprising thin flakes, a method for manufacturing the same and the use thereof as cosmetics and as a filler as mentioned in the following [1] to [6].

[1] A pigment comprising thin flakes where spherical silica particles having an average particle size of 20–400 nm are adhered on the surface of a flaky substrate having an average particle size of 0.5–10 $\mu$m and then the said surface of the flaky substrate adhered with spherical silica is further coated with ultrafine particles of titanium dioxide. The ultrafine titanium dioxide serves to form a thin glaze adhering the silica to the substrate; exfoliation of the spherical silica is thus suppressed.

[2] The pigment comprising thin flakes according to [1]. wherein the amount of the spherical silica particles is 30% by weight of less based upon the flaky substrate adhered with the spherical silica.

[3] The pigment comprising thin flakes according to [1] or [2], wherein the amount of the fine particles of titanium dioxide is 1–50% by weight based upon the pigment in thin flakes and the particle size of the fine particles of the said titanium dioxide is 50 nm, preferably 30 nm, or smaller.

[4] A method for the manufacture of the pigment comprising thin flakes according to any of [1]–[3], characterized in that, an aqueous solution of alkali is added to an aqueous suspension of the flaky substrate to make alkaline, a suspension of fine particles of spherical silica is added to the said alkaline suspension with heating and stirring, a part of the predetermined amount of aqueous solution of titanium salt is dropped thereinto to make pH 1.5–2.5 to adhere the spherical silica particles to the surface of the flaky substrate, the residual aqueous solution of titanium salt is added thereto keeping the pH at 1.5–2.5, then pH is raised to 5 and the resulting solid is filtered, washed with water, dried and calcined.

[5] A cosmetic agent containing the pigment comprising thin flakes according to any of [1]–[3].

[6] A use of the pigment comprising thin flakes according to any of [1]–[3] as a filler.

Basically, any of natural and synthetic substances may be used as a material for the flaky substrate which is used in the present invention but, in view of the use as a pigment, a substance having a high safety and a good durability such as heat resistance is preferred. To be more specific, natural mica, synthetic mica, mica titanium (mica in thin flakes which is coated with titanium oxide; this term is used in the same sense throughout the specification), talc, sericite, kaolin and alumina in thin flakes (including that which is coated with titanium oxide) may be exemplified and natural mica, synthetic mica, mica titanium, talc and sericite are preferred. Among them, natural mica, synthetic mica and mica titanium are more preferred.

With regard to the shape of those flaky substrates, the average particle size is recommended to be about 0.5–10 μm or, preferably, about 2–8 μm so that the size of the particles maintains a low frictional coefficient (MIU) suitably for use as cosmetics and, at the same time, hardly resulting in aggregation of the powder. When the particles of smaller than 0.5 μm are used, the product obtained by the present invention may be aggregated and is not preferred. As a result, it goes without saying that improvement in spreadability and soft focus effect is diminished. On the other hand, when the particles of larger than 10 μm are used, good slidability on the skin is diminished. The particles having such preferred sizes can be easily manufactured from natural or synthetic substance by means of a combination of pulverization and classification which are common to the persons skilled in the art. Some of the synthetic substance may be made into a predetermined size within the above range by controlling the growth rate of the crystals during the synthesis such as a hydrothermal process and a molten salt process. The commercially available ones having the above particle size may be easily used as well. Among those substrates in thin flakes, natural mica or that which is coated with titanium oxide (mica titanium) is particularly suitable as a substrate in view of a low cost and easy availability.

The spherical silica particles used in the present invention are easily available in the market. The particle size is decided based on the size (e.g., 0.5–10 μm ) of the above flaky substrate, by a relation with the aimed low frictional coefficient, etc. and particles having an average particle size of about 20 nm–400 nm, preferably about 40 nm–300 nm, more preferably 500 nm–300 nm are most suitable. When the particle size of the spherical silica is smaller, adhesion of the spherical silica onto the flaky substrate lowers whereby the spreadability is not optimal. As a result, a soft focus effect is not as great. On the other hand, when the particle size is larger, adhesion of the spherical silica particles onto the surface of the flaky substrate is good but there is lessened improvement in the spreadability and frictional coefficient (MIU) is not optimal. There is a tendency that, when the substrate particles in thin flakes having big particle size within the above range are used, it is preferred to use the spherical silica particles having the big size within the above range while, when the particle size of the flaky substrate itself becomes small, the spherical silica particles having small size are used accordingly. As a result, the larger the particle size of the spherical silica, the lower the frictional coefficient to the flaky substrate and the better the effect. When the spherical silica having a big particle size is used, an effect of lowering the frictional coefficient (MIU) is available with a small coating amount while, when the spherical silica particles become small, the effect of lowering the frictional coefficient is lessened.

Thus, as the adhering amount of the spherical silica particles increases, a lowering in the frictional coefficient (MIU) is noted in the initial stage and then approaches a minimum and, after that, the frictional coefficient gradually rises. Such a tendency is significant when the particle size of the spherical silica used is big and, when the particle size of the spherical silica is small, there is a tendency that the said minimum value is more difficult to achieve. That is presumably because, when the spherical silica particles having a small particle size are used, their unit surface area is large whereby the apparent contacting area with the flaky substrate becomes large resulting in a big frictional coefficient. In addition, the reason why the frictional coefficient gradually increases again after the frictional coefficient approaches a minimum value is presumably because the adhered spherical silica particles are aggregated each other whereby the contacting areas among the silica particles become large. In the present invention, such a phenomenon is taken into account, the spherical silica particles within a preferable range of average particle size of about 20–400 nm are appropriately selected by taking the soft focus effect and the spreadability with an object of making the adhered amount 30% by weight or less into consideration. Here, the value of MIU are those which are measured by "Tester for Frictional Feel, type KES-SE-DC" manufactured by Katotech K.K. according to the directed measuring conditions and the smaller the said value, the less the frictional coefficient or the more the spreading effect.

For example, in case mica having an average particle size of about 5 μm is used as a flaky substrate, the suitable amounts are, e.g., about 5–30% by weight and 5–20% by weight when the particle size of the spherical silica is about 70–400 nm and 40–50 nm, respectively.

Such spherical silica particles are sold in the market and are commercially available easily. (For example, Snowtex series manufactured by Nissan Chemical and silica for column chromatography manufactured by Merck.)

The pigment comprising thin flakes in accordance with the present invention is a pigment where titanium dioxide is coated on the surface of the flaky substrate to which the above spherical silica particles are adhered. As a result, adhesive properties of the spherical silica particles to the flaky substrate can be improved and, in addition, ultraviolet shielding effect and degree of whiteness can be increased as well.

With regard to a starting material for titanium dioxide in the present invention, anything may be used so far as it is a titanium salt compound. For example, an acidic salt such as titanium tetrachloride, titanyl sulfate or titanyl nitrate is used preferably for the purpose of lowering the pH during the manufacturing stage. In the present invention, a part of an aqueous solution of such a titanium salt may be substituted with a solution of zinc salt or of cerium salt so that the ultraviolet shielding ability or the ultraviolet shielding wave length are appropriately modified.

The following methods are adopted for the manufacture of the pigment comprising thin flakes of the present invention.

First, an aqueous suspension of the flaky substrate is prepared and an aqueous solution of alkali is added with heating (at about 70° C.) and stirring until the pH of the suspension becomes alkaline of 10 or higher or, preferably, 12 or higher. The reason why the pH is made alkaline is to avoid the isoelectric point (i.e., the pH where the surface charge becomes zero and aggregation is apt to take place) of the flaky substrate and to repulse the substrate in thin flaky substrate each other giving a dispersed state. Accordingly, it is necessary that the pH for resulting in such a dispersed state is appropriately changed depending upon the isoelectric point of the flaky substrate. For example, when natural mica is used as the flaky substrate, an appropriate pH is usually 12. It goes without saying that, when the substrate in flaky substrate having a high isoelectric point is used, the pH is to be made higher for maintaining the dispersibility while, when the isoelectric point is lower than natural mica, the pH becomes low and, usually, pH of around 10 is adopted.

After that, spherical silica particles are added to the suspension of the substrate in flaky substrate under such alkaline conditions. Under such a state that the flaky substrate and the spherical silica particles are well dispersed, an aqueous solution of the above titanium salt is added with stirring to lower the pH to 1.5–2.5. The surface charge of the flaky substrate and the spherical silica particles is made close to the isoelectric points of them (i.e. a repulsive force is lowered) whereby the flaky substrate and the spherical silica particles are adhered each other. This pH is to adhere the flaky substrate with the spherical silica particles at the points which are close to isoelectric points of them (under a state where the absolute values of the surface charge are close to each other) and also is a result of taking the pH of the hydrolysis reaction of titanium salt thereafter into consideration. In that case, it is also possible that a solution of a tin salt or the like is added and used as an agent to give a rutile type so that the crystalline form of titanium dioxide in the final product is not made the common anatase type but the rutile type. Then the residual predetermined amount of aqueous solution of titanium salt is added together with a simultaneous addition of the aqueous solution of alkali for keeping the pH constant whereby a hydrolyzed titanium product or the so-called titanium hydrate (a mixed state of hydroxide, adduct of oxide with water of crystallization, hydrate and oxide) is coated. It is also possible to adopt a manufacturing method where a part of the predetermined amount of aqueous solution of the titanium salt is previously hydrolyzed by heating to give a rutile type followed by coating whereby the crystalline form of the final titanium dioxide is made into a rutile type.

The amount of the titanium salt used including the amount for lowering the pH to 1.5–2.5 is 1–50% by weight to the final product based upon titanium oxide. This is because the titanium salt is hydrolyzed and adhered on the surface of the flaky substrate and the spherical silica whereby exfoliation of the spherical silica particles is suppressed and, at the same time, the ultraviolet shielding effect and degree of whiteness are improved. Such effects are lessened when the amount is less than 1% while, when it is more than 50%, the relative amount of the spherical silica particle is reduced and, therefore, the main object of the present invention which is a soft focus effect for wrinkle hiding achieved by the spherical silica particles is reduced. In the hydrolyzing reaction of the titanium salt, a manufacturing condition is selected to such an extent that the particle size of the final product which is titanium oxide is made about 30 nm or smaller. The said condition can be easily decided by an appropriate selection of the conventional condition for the manufacture of pigments such as adding speed, revolutions of the stirring blade and temperature. After completion of dropping of the predetermined amount of the aqueous solution of the titanium salt under a predetermined pH as such, the pH is adjusted to about 5 using an aqueous solution of alkali and the coated pigment in the reaction solution is filtered, washed with water for desalting, dried at usual temperature and finally calcined at about 600–900° C.

The pigment comprising thin flakes manufactured by the above method exhibits a soft focus effect, a spreadability (lower MIU) and an ultraviolet shielding effect, has an appropriate degree of whiteness and shows an excellent characteristic as a pigment for cosmetics. In addition, the pigment comprising thin flakes in accordance with the present invention can be used as a filler for resins and also can be used as printing ink or paint which are the uses for common pigments.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above or below, and of corresponding Japanese application No. 11-214927, filed Jul. 29, 1999 is hereby incorporated by reference.

EXAMPLES

Example 1

Mica (145 g) having an average particle size of 5 $\mu$m was suspended in 1,400 ml of water and heated up to 70° C. with stirring. A solution (about 3.0 ml) of 32% by weight of sodium hydroxide was added to the resulting aqueous suspension to adjust to pH 12. To the said suspension were supplied 40 g of 40% by weight suspension of colloidal silica particles (trade name: "Snowtex ZL"; average particle size: 70 nm; manufactured by Nissan Chemical) with stirring at the quantitative rate of 5 ml per minute. After that, about 100 ml of an aqueous solution of titanium tetrachloride having a concentration of 436 g/liter were prepared and supplied thereto at the quantitative rate of 2.5 ml per minute to lower the pH of the said aqueous suspension from 12 to 2. As a result of addition of titanium tetrachloride which was an acidic component, the spherical silica colloid particles were adhered onto the surface of the mica. The residual aqueous solution of titanium tetrachloride was similarly supplied to the said suspension keeping at pH 2 using an aqueous solution of 32% by weight of sodium hydroxide. After completion of supplementing of all of the aqueous solution of titanium tetrachloride, the pH was raised to 5 using an aqueous solution of 32% by weight of sodium hydroxide. After that, the product was filtered, washed with deionized water, dried at 110° C. and finally calcined at 700° C. to give a desired pigment of thin flakes. The resulting pigment of thin flakes contained 9.4% by weight of spherical silica particles and 11.9% by weight of titanium oxide and the particle size of the coated titanium oxide as measured by means of an SEM (scanning electron microscope) was not larger than 30 nm.

1) Measurement of Color Tone

[1] Preparation of Test Paper

Each one gram of the pigment in thin flakes of the present invention prepared in Example 1 and of the samples as shown in the following table was added to 9 g of a vinyl chloride medium containing 20% by weight of solid followed by mixing with stirring, the resulting dispersion was applied to a black-and-white test paper for measuring using a bar coater No. 20 and measurement of color tone was carried out as follows using this test paper.

[2] Measurement of Soft Focus

The diffuse reflection ratio (Y) on white color of the test paper prepared in the above [1] was measured using a three-dimensional spectrographic bending color difference meter (type GC-2000 manufactured by Nippon Denshoku Kogyo) where the value at angle of incidence was 45° and angle of reflection of light was 45° by a standard board for white diffuse reflection was defined 100 and the measurement was conducted using incident beam wherein angle of incidence of was 45° and angle of reflection of light was changed with an interval of 5°. The result is given in FIG. 1 in which an abscissa shows angle of reflection of light while an ordinate shows reflection intensity.

Y(−45°/30°) means the reflection intensity of the reflected beam at an angle of 30° to the normal line when light is incident at an opposite direction angle of 45° to a normal line.

It was ascertained from FIG. 1 that the pigment prepared in Example 1 showed low reflectance of light of regular reflection at 45°/45° as compared with mica and accordingly that the said pigment had a strong soft focus effect. Incidentally, in the table, Y values at (−45°/30°), (−45°/45°) and (−45°/60°) are shown.

[3] Degree of Whiteness

This is a value calculated from an expression of 100−$[(100-L)^2+a^2+b^2]^{1/2}$ in which L, a and b were measured using a three-dimensional color difference meter (type GC-3000A manufactured by Nippon Denshoku Kogyo).

[4] Hiding Power

This is a value calculated from an expression of $$\{Y(-45°/45°)\text{(on black paper)}/Y(-45°/45°)\text{(on white paper)}\}\times 100.$$

2) Measurement of Ultraviolet Shielding Property

A sample (0.5 g) was added to 9.5 g of a vinyl chloride-type medium containing 20% by weight of solid followed by mixing with stirring and the resulting dispersion was applied onto a glass plate using an applicator having a thickness of 120 $\mu$m. After drying, a transmittance of the resulting film at the ultraviolet wave length region of 300 nm (UVB) was measured by a spectrophotometer (type 228 manufactured by Hitachi). Accordingly, the less the numerals, the higher the UV shielding property.

Physical properties of the samples measured by the above-mentioned method are given in the following table.

TABLE 1

| | Physical Property of the Samples | | | | | | |
| Samples Used | Y(−45°/30°)* | Y(−45°/45°)* | Y(−45°/60°)* | Whiteness | Hiding Power | MIU | UV Shielding** |
| --- | --- | --- | --- | --- | --- | --- | --- |
| Example 1 | 60.7 | 85.2 | 85.2 | 89.2 | 6.8 | 0.42 | 15.0 |
| Comparative Example 1 (Mica) | 66.9 | 123.0 | 91.6 | 84.5 | 5.7 | 0.77 | 62.5 |
| Comparative Example 2 (Talc) | 61.6 | 86.3 | 84.5 | 92.5 | 5.0 | 0.57 | — |
| Comparative Example 3 (BLF) | 70.8 | 166.0 | 111.6 | 88.4 | 9.4 | 0.43 | — |

*on white paper;
**transmittance at 300 nm

In the table, each of the samples is as follows.

Mica: Average particle size being 5 $\mu$m (the same as the mica material used in Example 1)

Talc: Talc-L manufactured by Asada Seifun; average particle size being 6 $\mu$m.

BLF: Bismuth oxychloride (trade name: Biron LF 2000 manufactured by Rona)

MIU means a frictional coefficient (as measured by "Frictional Feel Tester, type KES-SE-DC" manufactured by Katotech KK)

It is apparent from the physical properties of the samples shown in Table 1 and also from FIG. 1 that, when the measuring angle (angle of reflection) was changed as 30°, 45° and 60° at the angle of incidence of 45°, the pigment of thin flakes according to the present invention showed little change in the reflection intensity and accordingly that it had a good so-called soft focus effect. In addition, the said pigment had good hiding power and degree of whiteness and, from the result of MIU, the said pigment showed a low sliding frictional coefficient, a good spreadability and a good ultraviolet shielding effect.

Application Examples

Application Example 1

Use as Cosmetics

A cosmetic agent (compact powder) having the following composition was prepared using the powder of thin flakes obtained in Example 1.

Composition:

| | |
|---|---|
| Pigment of thin flakes obtained in Example 1 | 25 parts by weight |
| Coloring pigment | 5 parts by weight |
| Lanolin | 3 parts by weight |
| Isopropyl myristate | q.s. |
| Magnesium stearate | 2 parts by weight |
| Talc | 50 parts by weight |

Application Example 2

Use as a Filler in Plastics

Composition:

| | |
|---|---|
| High-density polyethylene resin (pellets) | 100 parts by weight |
| Pigment in thin flakes obtained in Example 1 | 1 part by weight |
| Magnesium stearate | 0.1 part by weight |
| Zinc stearate | 0.1 part by weight |

The pellets according to the above compounding ratio were subjected to a dry blending and then to an injection molding.

According to Example 1, 9 samples of the pigment were further manufactured. The frictional coefficient (MIU) for all samples and the UV shielding effect (transparency in % at wavelength of 300 nm) for the samples of Examples 1 and 9 were measured. The best results were obtained for Example 9. Frictional coefficient (MIV) and transparency of the pigment have the best values.

TABLE 2

Results of the evaluation of MIU and UV shielding effect

| Run No. | Silica (Ave. particle size nm, and wt %) | | $TiO_2$ (wt %) | MIU × 10 − 1 | Transparency (%) at 300 nm |
|---|---|---|---|---|---|
| 1 | 70 nm, | 9.4 wt % | 11.9 wt % | 4.2 | 15.0 |
| 2 | 50 nm, | 9.7 wt % | 2.2 wt % | 4.93 | — |
| 3 | 70 nm, | 9.7 wt % | 2.2 wt % | 3.76 | — |
| 4 | 100 nm, | 9.7 wt % | 2.2 wt % | 3.73 | — |
| 5 | 300 nm, | 9.7 wt % | 2.2 wt % | 3.41 | — |
| 6 | 70 nm, | 9.3 wt % | 6.3 wt % | 4.08 | — |
| 7 | 70 nm, | 8.7 wt % | 11.9 wt % | 4.75 | — |
| 8 | 70 nm, | 5.1 wt % | 2.3 wt % | 3.93 | — |
| 9 | 300 nm, | 9.7 wt % | 5.0 wt % | 2.87 | 12.4 |
| 10 | 300 nm, | 5.0 wt % | 2.2 wt % | 3.37 | — |

ADVANTAGES OF THE INVENTION

Figure 1:
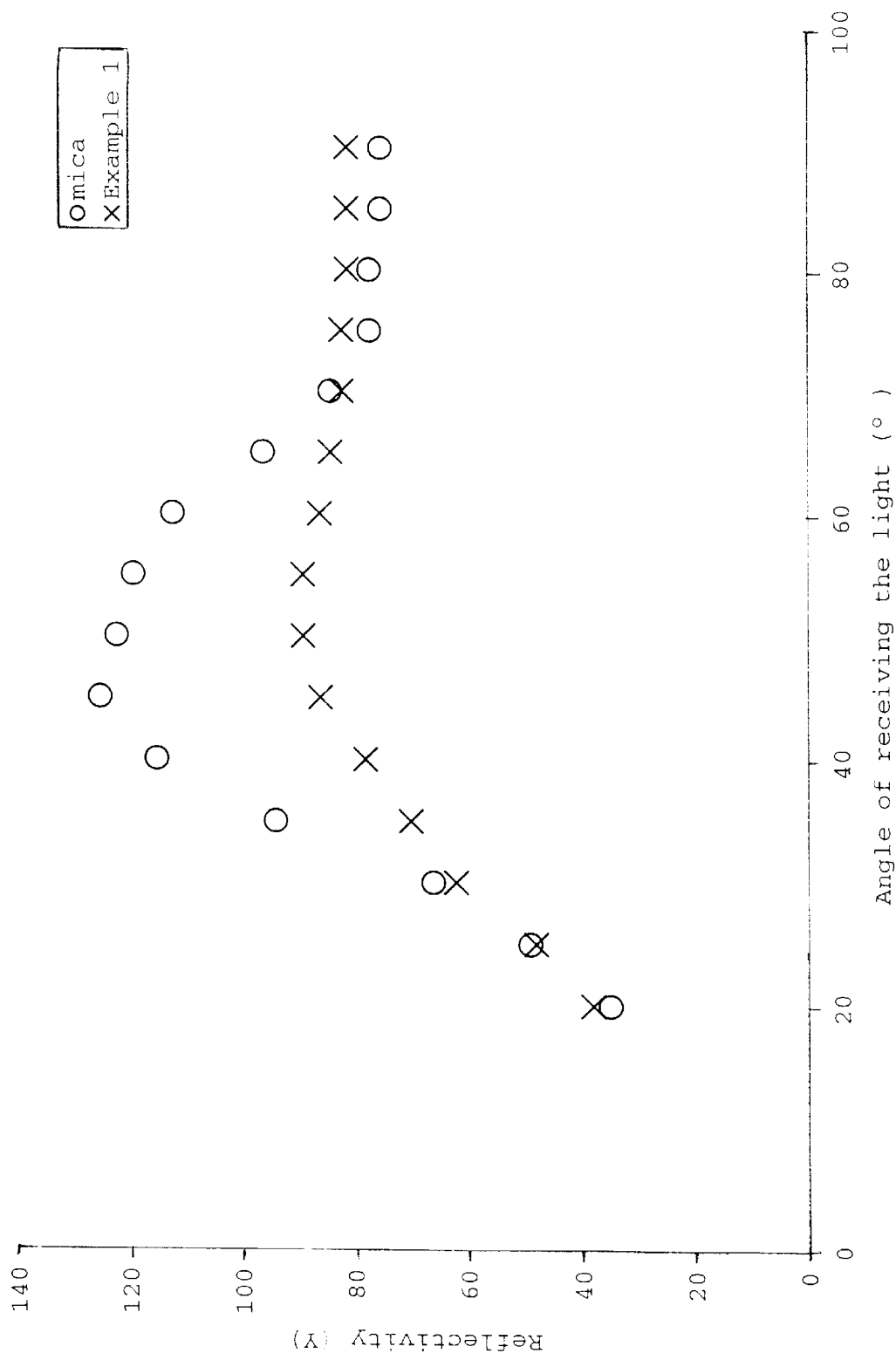
FIG. 1 is a graph showing a distribution of reflected light as measured for the pigment of thin flakes of the present invention and for mica.

As mentioned hereinabove, the pigment in thin flakes according to the present invention has a soft focus effect, shows a low frictional coefficient (MIU), has both appropriate degree of whiteness and ultraviolet shielding property and exhibits excellent characteristics as a pigment especially for cosmetics.

What is claimed is:

1. A pigment comprising spherical silica particles adhered on the surface of a flaky substrate, said spherical silica particle-adhered surface of the flaky substrate being coated thereover with ultrafine particles of titanium dioxide.

2. The pigment according to claim 1, wherein the amount of the spherical silica particles is up to 30% by weight based upon the flaky substrate adhered with the spherical silica.

3. The pigment according to claim 2, wherein the amount of the spherical silica particles is up to 5 to 30% by weight based upon the flaky substrate adhered with the spherical silica.

4. The pigment according to claim 2, wherein the amount of the spherical silica particles is up to 5 to 20% by weight based upon the flaky substrate adhered with the spherical silica.

5. A cosmetic agent containing a pigment according to claim 2.

6. The pigment according to claim 1, wherein the amount of the ultrafine particles of titanium dioxide is 1–50% by weight based upon the pigment and the particle size of the fine particles of said titanium dioxide is up to 50 nm.

7. The pigment according to claim 1, wherein the flaky substrate has a particle size of 2–8 µm.

8. The pigment according to claim 1, which the spherical silica has an average particle size of 40–300 nm.

9. The pigment according to claim 1, which the amount of titanium dioxide is 5–30% by weight based on the pigment and the particle size of the spherical silica is 70–400 nm.

10. A cosmetic agent containing a pigment according to claim 9.

11. The pigment according to claim 1, which the amount of titanium dioxide is 5–20% and the particle size of the spherical silica is 40–50 nm.

12. A method for the manufacture of the pigment according claim 1, comprising adding an aqueous solution of alkali to an aqueous suspension of the flaky substrate to make the suspension alkaline, adding a suspension of fine particles of spherical silica to the alkaline suspension with heating and stirring, adding a part of a predetermined amount of aqueous solution of titanium salt is to reach a pH of 1.5–2.5, adhering the spherical silica particles to surfaces of the flaky substrate, adding residual aqueous solution of titanium salt while keeping the pH at 1.5–2.5, then raising the pH to 5.

13. The process according to claim 12, further comprising filtering resulting solid, washing with water, drying and calcining.

14. A cosmetic agent containing a pigment according to claim 1.

15. A resin containing a filler which is a pigment according to claim 1.

16. A pigment according to claim 1, wherein the spherical silica has an average particle size of 20–40 nm and the flaky substrate has an average particle size of 0.5–10 µm.

* * * * *